US006815435B2

(12) United States Patent
Takahashi et al.

(10) Patent No.: US 6,815,435 B2
(45) Date of Patent: Nov. 9, 2004

(54) PHARMACEUTICAL COMPOSITIONS CONTAINING DDS COMPOUNDS

(75) Inventors: Masayuki Takahashi, Edogawa-ku (JP); Shuichi Sugie, Takatsuki (JP); Masahito Takeuchi, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/332,706

(22) PCT Filed: Jul. 11, 2001

(86) PCT No.: PCT/JP01/06020

§ 371 (c)(1),
(2), (4) Date: Jan. 13, 2003

(87) PCT Pub. No.: WO02/05855

PCT Pub. Date: Jan. 24, 2002

(65) Prior Publication Data

US 2003/0148931 A1 Aug. 7, 2003

(30) Foreign Application Priority Data

Jul. 13, 2000 (JP) ....................................... 2000-213083

(51) Int. Cl.[7] .................... A61K 31/715; A61K 31/721; A61K 38/14; C08B 37/02

(52) U.S. Cl. ............................ 514/59; 514/54; 514/53; 514/8; 536/112; 536/123.1; 536/123.12; 530/322; 530/330

(58) Field of Search ................................ 514/59, 53, 8; 536/112, 123.1; 530/322, 330

(56) References Cited

U.S. PATENT DOCUMENTS 4,418,058 A * 11/1983 Hirai et al.
4,876,244 A * 10/1989 Umezawa et al.
6,436,912 B1 * 8/2002 Inoue et al.

FOREIGN PATENT DOCUMENTS

| | | | |
|---|---|---|---|
| EP | 857484 A1 | | 8/1998 |
| WO | WO-97-29782 | * | 8/1997 |
| WO | WO 97/29782 A1 | | 8/1997 |
| WO | WO 97/45135 A1 | | 12/1997 |
| WO | WO 97/46260 A1 | | 12/1997 |
| WO | WO-97-451135 | * | 12/1997 |
| WO | WO 00/18401 A1 | | 4/2000 |

OTHER PUBLICATIONS

International Search Report dated Oct. 9, 2001.

* cited by examiner

*Primary Examiner*—Elli Peselev
*Assistant Examiner*—Michael C. Henry
(74) *Attorney, Agent, or Firm*—Sughrue Mion, PLLC

(57) ABSTRACT

A pharmaceutical composition having an ensured preservation stability, which contains a compound, wherein a polysaccharide derivative having a carboxyl group is bonded to a camptothecin derivative via a spacer or without mediated by any spacer, and a sugar or a sugar alcohol optionally together with a pH-adjusting substance.

18 Claims, No Drawings

PHARMACEUTICAL COMPOSITIONS CONTAINING DDS COMPOUNDS

TECHNICAL FIELD

This invention relates to a freeze-dried preparation of a pharmaceutical composition containing a drug delivery system (DDS) compound wherein a polysaccharide derivative having a carboxyl group is bonded to a camptothecin derivative via a peptide chain (a spacer) or without mediated by any spacer.

BACKGROUND ART

When administered to the whole body, many anti-tumor agents are distributed into various cells and tissues in the whole body and act as cytotoxins on normal cells and tissues too. As a result, there arises a serious problem of side effects causing, for example, diarrhea, fever, vomiting and hair removal at an extremely high frequency. To overcome this problem, it has been required to develop means of delivering an anti-tumor agent efficiently and selectively to a tumor site.

As an example of such means, there is reported a DDS technique wherein a polysaccharide derivative, which is used as a drug carrier, is bonded to an anti-tumor agent to thereby delay the disappearance of the anti-tumor agent in the blood and enhance the directivity toward the cancer tissue (WO 094/19376, WO 094/19376, JP-B-7-84481; the term "JP-B" as used herein means an "examined Japanese patent publication").

Among DDS compounds with the use of polysaccharide derivatives as drug carriers, a DDS compound wherein a polysaccharide derivative obtained by polyalcoholizing carboxymethyldextran is used as a drug carrier and bonded to a camptothecin derivative (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13 (9H, 15H)-dione (hereinafter sometimes referred to as the compound A) via a peptide chain has an extremely excellent tumor selectivity and anti-tumor activity. Thus, attempts are now underway to clinically test this compound.

However, preparations obtained by freeze-drying the above-described DDS compounds suffer from a problem of having very poor preservation stability, since the molecular weight thereof is increased during preservation, thereby causing changes in the form of the preparations and worsening the re-dissolution properties thereof.

The present invention provides pharmaceutical compositions containing a drug delivery system (DDS) compound wherein a polysaccharide derivative having a carboxyl group is bonded to a camptothecin derivative via a peptide chain (a spacer) or without mediated by any spacer to thereby ensure high preservative stability of the compound.

DISCLOSURE OF INVENTION

As the results of intensive studies, the inventors have found out that an increase in the molecular weight of the above-described compound can be inhibited by adding to the compound a sugar or a sugar alcohol together with, if needed, a pH-adjusting substance and then freeze-drying.

Accordingly, the present invention relates to a pharmaceutical composition containing a drug delivery system (DDS) compound, wherein a polysaccharide derivative having a carboxyl group is bonded to a camptothecin derivative via a peptide chain (a spacer) or without mediated by any spacer, and a sugar or a sugar alcohol.

More particularly, the present invention relates to a pharmaceutical composition containing a compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione without mediated by any spacer and one or more sugars or sugar alcohols selected from the group consisting of maltose, glucose, lactose, trehalose, saccharose, mannitol, inositol, galactose, ribose, xylose, mannose, sucrose, cellobiose, raffinose and maltotriose.

The present invention further relates to the above-described pharmaceutical composition containing a compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[2-b]quinoline-10,13(9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione without mediated by any spacer, one or more sugars or sugar alcohols selected from the group consisting of maltose, glucose, lactose, trehalose, saccharose, mannitol, inositol, galactose, ribose, xylose, mannose, sucrose, cellobiose, raffinose and maltotriose, and a pH-adjusting substance.

Further, it relates to the above-described pharmaceutical composition wherein the polysaccharide derivative having a carboxyl group is a carboxy($C_{1-4}$ alkyl)dextran polyalcohol.

Moreover, it relates to the above-described pharmaceutical composition wherein the polysaccharide derivative having a carboxyl group is carboxymethyldextran polyalcohol.

Further, it relates to the above-described pharmaceutical composition wherein the weight-average molecular weight of the carboxymethyldextran polyalcohol ranges from 50,000 to 500,000.

Moreover, it relates to the above-described pharmaceutical composition wherein the carboxymethyldextran polyalcohol has a degree of carboxymethylation of from 0.2 to 0.5.

Further, it relates to the above-described pharmaceutical composition wherein the spacer consists of amino acids represented by the amino acid sequence (N end)-Gly-Gly-Phe-Gly-(C end).

Moreover, it relates to the above-described pharmaceutical composition wherein (1S,9S) -1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione is introduced in an amount of 2 to 10% by weight based on the weight of a compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13 (9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5-fluoro-2,3-dihydro-9-hydroxy- 4-methyl-1H,12H-benzo[de]pyrano[3',4':6,7]indolizino[1,2-b]quinoline-10,13(9H,15H)-dione without mediated by any spacer.

Further, it relates to the above-described pharmaceutical composition wherein the sugar or sugar alcohol is maltose.

Moreover, it relates to the above-described pharmaceutical composition wherein the content of maltose, in terms of the weight as maltose monohydrate, is thrice or more as much as the weight of the compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione without mediated by any spacer.

Further, it relates to a wherein the pH-adjusting substance is hydrochloric acid or sodium hydroxide.

Moreover, it relates to the above-described pharmaceutical composition which has a pH value of about 5.5 to 9.0.

Further, it relates to the above-described pharmaceutical composition which has a pH value of 6.0 to 9.0.

Moreover, it relates to the above-described pharmaceutical composition which has a pH value of 6.3 to 7.0.

Further, it relates to the above-described pharmaceutical composition containing a compound wherein carboxymethyldextran polyalcohol is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione via a spacer consisting of amino acids represented by the amino acid sequence (N end)-Gly-Gly-Phe-Gly-(C end) and maltose, wherein the molecular weight of the carboxymethyldextran polyalcohol ranges from 50,000 to 500,000, the carboxymethyldextran polyalcohol has a degree of carboxymethylation of from 0.2 to 0.5, (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione is introduced in an amount of 2 to 10% by weight based on the weight of the compound, the content of maltose, in terms of the weight as maltose monohydrate, is thrice or more as much as the weight of the compound, and the pH value is from 6.0 to 9.0.

Moreover, it relates to the above-described pharmaceutical composition containing a compound wherein carboxymethyldextran polyalcohol is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione via a spacer consisting of amino acids represented by the amino acid sequence (N end)-Gly-Gly-Phe-Gly-(C end), maltose and a pH-adjusting substance, wherein the molecular weight of the carboxymethyldextran polyalcohol ranges from 50,000 to 500,000, the carboxymethyldextran polyalcohol has a degree of carboxymethylation of from 0.2 to 0.5, (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione is introduced in an amount of 2 to 10% by weight based on the weight of the compound, the content of maltose, in terms of the weight as maltose monohydrate, is thrice or more as much as the weight of the compound, the pH-adjusting substance is hydrochloric acid or sodium hydroxide, and the pH value is from 6.0 to 9.0.

Further, it relates to a freeze-dried preparation containing the above-described pharmaceutical compositions.

The pharmaceutical composition according to the present invention is characterized by containing a compound wherein a polysaccharide derivative having a carboxyl group is bonded to the compound A via a spacer consisting of one amino acid or a spacer consisting of 2 to 8 amino acids bonded to each other via peptide bonds, or a compound wherein a polysaccharide derivative having a carboxyl group is bonded to the compound A without mediated by any spacer. The bond between the polysaccharide derivative or the spacer and the compound A is formed by reacting (for example, dehydrocondensing) a reactive functional group in the compound A with a reactive functional group in the polysaccharide derivative or the spacer. Although the compound A can be synthesized by a method described in JP-A-5-59061, the invention is not restricted thereto.

The compound A is bonded to the carboxyl group of the polysaccharide derivative, the N-terminal amino group or the C-terminal carboxyl group of the spacer, a reactive functional group in an amino acid constituting the spacer, or the like. As preferable examples of the spacer, amino acid spacers and peptide spacers described in WO97/46260, etc. may be cited. In particular, a spacer consisting of amino acids represented by the amino acid sequence (N end)-Gly-Gly-Phe-Gly-(C end) is preferable therefor.

The compound A or the spacer can be bonded to the carboxyl group of the polysaccharide derivative having a carboxyl group generally by forming an acid-amide bond between the amino group of the compound A or the N-terminal amino group of the spacer and the carboxyl group of the polysaccharide derivative having a carboxyl group. To form the acid amide bond, it is preferable to use a dehydrocondensing agent commonly employed in synthesizing peptide chains, for example, N,N'-dicyclohexyl carbodiimide (DCC) or 1-ethoxycarbonyl-2-ethoxy-1,2-dihydroxyquinoline (EEDQ). The compound A may be bonded to the spacer by the dehydrocondensation of the amino group of the compound A and the carboxyl group of the spacer with the use of a common condensing agent such as DCC.

The polysaccharide derivative having a carboxyl group constituting the compound contained in the pharmaceutical composition according to the invention maybe an arbitrary one, so long as it is a polysaccharide or a derivative obtained by chemically or biologically modifying the same and has a carboxyl group in its molecule. For example, it is appropriate to use polysaccharides such as hyaluronic acid, pectic acid, alginic acid, chondroitin and heparin, polysaccharide derivatives obtained by carboxy($C_{1-4}$)alkylating a part or all of the hydroxyl groups of polysaccharides such as pullulan, dextran, mannan, chitin, inulin, levan, xylan, araban, mannoglucan and chitosan, and polysaccharide derivatives obtained by forming an ester bond of a carboxyl group of polysaccharides. It is also possible to use polysaccharide derivatives obtained by polyalcoholizing the above-described polysaccharides and then introducing a functional group having a carboxyl group thereinto.

Among these polysaccharide derivatives, it is preferable to use a carboxy($C_{1-4}$ alkyl)dextran polyalcohol. Although the degree of polyalcoholization of the carboxy($C_{1-4}$ alkyl) dextran polyalcohol is not particularly restricted, it is preferable that the dextran polyalcohol constituting the carboxy ($C_{1-4}$ alkyl)dextran polyalcohol is a dextran polyalcohol obtained by treating dextran under such conditions as allowing substantially complete polyalcoholization. For example, it is favorable that dextran is treated successively with sodium periodate in large excess and sodium borohydride in large excess.

The dextran to be used as the starting material is not particularly restricted in type. Although the molecular weight of the dextran is not particularly restricted too, it is preferable to use dextran having a molecular weight of about 500,000 such as Dextran T500 (manufactured by Pharmacia). As the $C_{1-4}$ alkyl constituting the carboxy($C_{1-4}$ alkyl) group, use may be made of linear or branched $C_{1-4}$ alkyls such as methyl, ethyl, n-propyl, isopropyl, n-butyl and sec-butyl groups. It is preferable to use a methyl group. The carboxyalkylation may be carried out by, for example, a method described in WO97/46261, though the invention is not restricted thereto.

The degree of carboxyalkylation to the hydroxyl group in the dextran polyalcohol ranges, for example, from 0.01 to 2.0, preferably from 0.1 to 1.0 and still preferably from 0.2 to 0.5 per constituent saccharide residue, though the present invention is not restricted thereto. The degree of carboxyalkylation can be determined by measuring the electric charge per unit molecular weight by the capillary electrophoresis method, etc.

The weight-average molecular weight of the carboxy($C_{1-4}$ alkyl)dextran polyalcohol ranges from about 5,000 to 1,000,000, preferably from about 50,000 to 500,000, when determined by the gel filtration method with the use of pullulan as the standard. The pullulan to be used as the standard is available from, for example, Shodex. The weight-average molecular weight can be determined by the GPC-RI (gel permeation chromatograph refractive index) method (Analytical Biochem., 147, (1985), pp. 387–395), the GPC-LALLS (gel permeation chromatograph low-angle laser light scattering) method (J. Chromatography, 506, (1990), pp. 409–416), the viscosity measurement method, etc.

In the compound contained in the pharmaceutical composition according to the present invention, the content of the compound A to be introduced into the polysaccharide derivative having a carboxyl group should be appropriately determined by taking drug effect, toxicity, etc. into consideration. The content of the compound A may range from 0.1 to 30% by weight, preferably from 1 to 15% by weight and more preferably from 2 to 10% by weight based on the weight of the above-described compound. The content of the compound A introduced into the polysaccharide derivative having a carboxyl group can be easily determined by, for example, absorption spectrophotometry.

It is preferable that the pharmaceutical composition according to the present invention contains a sugar or a sugar alcohol. Examples of the sugar or sugar alcohol include maltose, glucose, lactose, trehalose, saccharose, mannitol, inositol, galactose, ribose, xylose, mannose, sucrose, cellobiose, raffinose and maltotriose. Either one of these sugars and sugar alcohols or a combination of two or more thereof can be used. Among all, it is preferable to use maltose alone. Although the content of maltose is not particularly restricted, the content of maltose, in terms of the weight as maltose monohydrate, is preferably 3 parts by weight or more, more preferably 3.3 parts by weight or more, per part by weight of the compound contained in the pharmaceutical composition according to the invention. Although the upper limit of the maltose content is not particularly restricted, it is preferable that its concentration does not exceed the saturated solubility of maltose.

By adding the sugar or sugar alcohol, the preservation stability of the pharmaceutical composition according to the invention can be elevated. In case where a freeze-dried preparation, which contained the compound alone contained in the pharmaceutical composition of the present invention without any sugar or sugar alcohol, was preserved for a definite period of time and then the molecular weight was determined by the GPC-RI method, the GPC-LALLS method or the like, the weight-average molecular weight was increased with the passage of time. With the increase in the weight-average molecular weight, the freeze-dried preparation shrunk and suffered from a serious decrease in the re-dissolution properties. This increase in the weight-average molecular weight and changes in the properties of the preparation in association therewith were not observed in case where the polysaccharide derivative having a carboxyl group was preserved alone in the same manner. Therefore, it was assumed that these changes were caused by the compound A bonded to the polysaccharide derivative having a carboxyl group directly or via the spacer.

J. G. Shiah et al. suggest that the interaction among hydrophobic molecules bonded to a water-soluble polymer causes aggregation and association (Drug Delivery, 5(1998) pp. 119–126).

It is assumed that the hydrophobic interaction among molecules of the compound A would induce the aggregation and association of molecules, thereby increasing the molecular weight. It is also estimated that, in case where a sugar or a sugar alcohol is added, the sugar or sugar alcohol is located among the compound A molecules and thus inhibits the hydrophobic interaction, etc. among the compound A molecules. It is desirable that the substance located among the compound A molecules undergoes no interaction with the compound A. For example, it is considered that sugars or sugar alcohols, which are hydrophilic compounds, scarcely interact with the compound A. It is therefore desirable to add these compounds to ensure the preservation stability of the pharmaceutical composition according to the present invention.

From the viewpoint of preservation stability, it is preferable that the pH value of the pharmaceutical composition according to the present invention is maintained at 6.0 to 9.0. When preserved at pH 5.3, a change in the molecular weight and an increase in the degree of dispersion of the compound contained in the pharmaceutical composition of the present invention were observed. In particular, the degree of dispersion was remarkably increased. An increase in the degree of dispersion indicates that the molecular weight of the compound varies more broadly.

On the other hand, the compound contained in the pharmaceutical composition according to the present invention has the compound A, which is a camptothecin derivative, as its partial structure. Since the lactone ring in the compound A is opened under alkaline conditions, it is considered that the drug effect thereof is worsened. It is therefore preferable that the pH value of the pharmaceutical composition of the invention is maintained at about 5.5 to 9.0, more preferably at about 6.0 to 9.0 and most preferably at about 6.3 to 7.0. This pH value of the pharmaceutical composition means a pH value in the case of an aqueous solution. When the pharmaceutical composition is a freeze-dried preparation, it means a pH value of the aqueous solution of the freeze-dried preparation redissolved in water. The term "degree of dispersion" as used herein means the value determined by dividing weight-average molecular weight by number-average molecular weight.

To maintain the pH value within the range as specified above, the pharmaceutical composition of the present invention further contains a pH-adjusting substance in some cases. Examples of the pH-adjusting substance include acidic substances such as hydrochloric acid, acetic acid, sodium acetate, ascorbic acid, sodium ascorbate, phosphoric acid, sodium monohydrogenphosphate, sodium dihydrogenphosphate, citric acid and sodium citrate, and basic substances such as sodium hydroxide, trishydroxymethylaminomethane, glycine, ammonium chloride and triethanolamine. Either one of these substances or a combination of two or more thereof may be used. Among these pH-adjusting substances, it is preferable to use hydrochloric acid or sodium hydroxide alone.

The pharmaceutical composition according to the present invention may be in the form of a mixture wherein the compound consisting of the polysaccharide derivative having a carboxyl group bonded to the compound A via a spacer consisting of one amino acid or a spacer consisting of 2 to 8 amino acids bonded to each other via peptide bonds, or a compound consisting of the polysaccharide derivative having a carboxyl group bonded to the compound A without mediated by any spacer is merely mixed with a sugar or a sugar alcohol optionally together with a pH regulator. Alternatively, the pharmaceutical composition may be in a dosage form publicly known per se such as an aqueous preparation or a freeze-dried preparation. The aqueous preparation is exemplified by an aqueous injection prepared by sterilely filtering the pharmaceutical composition and an aqueous injection prepared by dissolving the pharmaceutical composition which has been once freeze-dried. The freeze-dried preparation may be produced by a method publicly known per se without restriction.

The present invention will be illustrated in greater detail with reference to the following Examples, but it is not intended that the invention be limited thereto. The term "DDS compound A" as used in these examples means a compound wherein the compound A is bonded to carboxymethyldextran polyalcohol via a spacer represented by the amino acid sequence (N end)-Gly-Gly-Phe-Gly-(C end).

BEST MODE FOR CARRYING OUT INVENTION

EXAMPLE 1

Change in Molecular Weight of DDS Compound A in Freeze-Dried DDS Compound A Preparation Containing Sugar A 10 mg/ml aqueous solution of the DDS compound A (A), a 10 mg/ml aqueous solution of the DDS compound A containing 2% by weight of maltose monohydrate (B), and a 10 mg/ml aqueous solution of the DDS compound A containing 10% by weight of maltose monohydrate (C) were freeze-dried and then preserved at 40° C. over a definite period of time. Then the weight-average molecular weight of the DDS compound A was determined by the GPC-LALLS method.

Thus, it was clarified that the change in the molecular weight of the DDS compound A could be prevented by adding the sugar.

TABLE 1

Change in molecular weight of DDS compound A in freeze-dried state

| Preservation conditions | Freeze-dried preparation A (no filler) | Freeze-dried preparation B (2 wt % of maltose) | Freeze-dried preparation C (10 wt % of maltose) |
|---|---|---|---|
| Initiation | $308 \times 10^3$ | $275 \times 10^3$ | $293 \times 10^3$ |
| 40° C., 9 days | $536 \times 10^3$<br>174% | N.P. | N.P. |
| 40° C., 3 weeks | N.P. | $328 \times 10^3$<br>119% | $318 \times 10^3$<br>109% |

Upper: weight-average molecular weight.
Lower: ratio (%) to initiation value.
N.P.: not performed.

EXAMPLE 2

Change in Molecular Weight of DDS Compound A in Freeze-Dried DDS Compound A Preparation Containing Sugar or Sugar Alcohol 10 mg/ml aqueous solutions of the DDS compound A respectively containing 3% by weight of maltose monohydrate (A), mannitol (B) and lactose (C) were freeze-dried and preserved at 40° C. over a definite period of time. Then the weight-average molecular weight of the DDS compound A was determined by the GPC-LALLS method.

Thus, it was clarified that the change in the molecular weight of the DDS compound A could be prevented by adding the sugar or sugar alcohol and maltose showed the highest preventive effect.

TABLE 2

Change in molecular weight of DDS compound A in freeze-dried state

| Preservation conditions | Freeze-dried preparation A (maltose) | Freeze-dried preparation B (mannitol) | Freeze-dried preparation C (lactose) |
|---|---|---|---|
| Initiation | $324 \times 10^3$ | $333 \times 10^3$ | $330 \times 10^3$ |
| 40° C., 2 weeks | $353 \times 10^3$<br>109% | $1050 \times 10^3$<br>315% | $411 \times 10^3$<br>125% |

Upper: weight-average molecular weight.
Lower: ratio (%) to initiation value.

EXAMPLE 3

Effect of Maltose Content of Preventing Change in Molecular Weight 10 mg/ml aqueous solutions of the DDS compound A containing 1, 3, 10 and 30 mg/ml of maltose monohydrate were freeze-dried and then preserved at 40° C. over a definite period of time. Then the weight-average molecular weight of the DDS compound A was determined by the GPC-LALLS method.

Thus, it was clarified that a remarkable effect of preventing the change in the molecular weight of the DDS compound A was achieved by adding 30 mg/ml or more of maltose per 10 mg/ml of the DDS compound A (i.e., thrice or more as much as the DDS compound A). A similar preventive effect was observed by adding maltose in an amount 10 times as much.

TABLE 3

Effect of maltose content of preventing change in molecular weight

| Preservation | Freeze-dried preparation Maltose concentration | | | |
|---|---|---|---|---|
| Conditions | 1 mg/ml | 3 mg/ml | 10 mg/ml | 30 mg/ml |
| Initiation | $320 \times 10^3$ | $327 \times 10^3$ | $342 \times 10^3$ | $324 \times 10^3$ |
| 40° C., 2 weeks | $1110 \times 10^3$<br>347% | $536 \times 10^3$<br>164% | $441 \times 10^3$<br>129% | $353 \times 10^3$<br>109% |
| 40° C., 1 month | N.P. | N.P. | N.P. | $372 \times 10^3$<br>115% |

Upper: weight-average molecular weight.
Lower: ratio (%) to initiation value.
N.P.: not performed.

EXAMPLE 4

Effect of Maltose Content on the Appearance of Freeze-Dried Products 10 mg/ml aqueous solutions of the DDS compound A containing 30 and 33 mg/ml of maltose monohydrate were freeze-dried and then the appearance of each freeze-dried product was observed.

In case of the solution with the maltose concentration of 30 mg/ml, as a result, 8.4% of freeze-dried products having a different (scaly) appearance was formed. In contrast thereto, few freeze-dried product with the scaly appearance was formed in case of the solution with the maltose concentration of 33 mg/ml. Namely, it is particularly preferable to add maltose monohydrate in an amount 3.3 times by weight or more as much as the DDS compound A.

TABLE 4

Result of examination on appearance of freeze-dried product

| | Freeze-dried preparation Maltose concentration | |
|---|---|---|
| Appearance | 30 mg/ml | 33 mg/ml |
| Products with normal appearance | 91.5% | 99.2% |
| Products with scaly appearance | 8.4% | 0.6% |
| Others | 0.1% | 0.2% |

EXAMPLE 5 pH-Dependency of Change in Molecular Weight of DDS Compound A

Maltose monohydrate was added to a 10 mg/ml aqueous solution of the DDS compound A to give a concentration of 30 mg/ml. Then the pH value was adjusted to 5.3 to 8.5 by using hydrochloric acid or sodium hydroxide. These solutions were freeze-dried and preserved at 40° C. over a definite period of time. Then the change in the weight-average molecular weight and the change in the degree of dispersion of the DDS compound A were measured by the GPC-LALLS method.

As a result, the samples of pH 6.3 and pH 7.0 was showed the smallest changes in molecular weight and the degree of dispersion, i.e., being the most stable. The samples of pH 7.2 and pH 8.5 showed each an increase in molecular weight but little change in the degree of dispersion. At pH 5.3, both of molecular weight and the degree of dispersion were largely changed.

Accordingly, it is preferable to regulate the pH value of the DDS compound A in the state of an aqueous solution to 5.5 or above, more preferably from 6.0 to 9.0 and most preferably from 6.3 to 7.0.

TABLE 5

Effect on change in molecular weight

| Preservation | Freeze-dried Product PH | | | | |
|---|---|---|---|---|---|
| conditions | 5.3 | 6.3 | 7.0 | 7.2 | 8.5 |
| Initiation | $361 \times 10^3$ | $363 \times 10^3$ | $360 \times 10^3$ | $348 \times 10^3$ | $349 \times 10^3$ |
| 40° C., 1 month | $333 \times 10^3$<br>92% | $341 \times 10^3$<br>94% | $365 \times 10^3$<br>101% | $457 \times 10^3$<br>131% | $414 \times 10^3$<br>119% |

Upper: weight-average molecular weight.
Lower: ratio (%) to initiation value.

TABLE 6

Effect on change in the degree of dispersion

| Preservation | Freeze-dried Product PH | | | | |
|---|---|---|---|---|---|
| conditions | 5.3 | 6.3 | 7.0 | 7.2 | 8.5 |
| Initiation | 1.4 | 1.4 | 1.4 | 1.5 | 1.5 |
| 40° C., 1 month | 2.4 | 1.6 | 1.6 | 1.7 | 1.7 |

Degree of dispersion: value determined by dividing weight-average molecular weight by number-average molecular weight.

INDUSTRIAL APPLICABILITY

As discussed above, the pharmaceutical compositions according to the invention are usable as freeze-dried antitumor preparation which are excellent in preservation stability.

What is claimed is:

1. A pharmaceutical composition containing a compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5-fluoro-2, 3-dihydro-9-hydroxy-4-methyl-1H,12H-benzo[de]pyrano[3',4':6,7]indolizino[1,2-b]quinoline-10,13(9H,15H)-dione without mediated by any spacer and maltose, in which molecular weight increase and change in appearance of the compounds are reduced during preservation of the compound.

2. A pharmaceutical composition containing a compound wherein a polysaccharide derivative having a carboxyl group is bonded to (1S,9S)-1-amino-9-ethyl-5-fluoro -2,3-dihydro-9-hydroxy-4-methyl-1H,12H-benzo[de]pyrano[3',4':6,7]indolizino[1,2-b]quinoline-10,13(9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5- fluoro -2,3-dihydro-9-hydroxy-4-methyl-1H,12H-benzo[de]pyrano[3',4':6,7]indolizino[1,2-b]quinoline-10,13(9H,15H)-dione without mediated by any spacer, maltose, and a pH-adjusting substance, in which molecular weight increase and change in appearance of the compounds are reduced during preservation of the compound.

3. A pharmaceutical composition as claimed in claim 1 or 2 wherein said polysaccharide derivative having a carboxyl group is a carboxy($C_{1-4}$ alkyl)dextran polyalcohol.

4. A pharmaceutical composition as claimed in claim 1 or 2 wherein said polysaccharide derivative having a carboxyl group is carboxymethyldextran polyalcohol.

5. A pharmaceutical composition as claimed in claim 4 wherein the weight-average molecular weight of said carboxymethyldextran polyalcohol ranges from 50,000 to 500,000.

6. A pharmaceutical composition as claimed in claim 4 wherein said carboxymethyldextran polyalcohol has a degree of carboxymethylation of from 0.2 to 0.5.

7. A pharmaceutical composition as claimed in claim 1 or 2 wherein said spacer consists of amino acids represented by the amino acid sequence (N end)-Gly-Gly-Phe-Gly-(C end).

8. A pharmaceutical composition as claimed in claim 1 or 2 wherein (1S,9S)-1-amino-9-ethyl-5-fluoro-2,3-dihydro-9-hydroxy-4-methyl-1H,12H-benzo [de]pyrano[3',4':6,7]indolizino[1,2-b]quinoline-10,13(9H,15H)-dione is introduced in an amount of 2 to 10% by weight based on the weight of a compound wherein a polysaccharide derivative having a carboxyl group is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5-fluoro -2,3-dihydro-9-hydroxy-4-methyl-1H,12H-benzo[de]pyrano[3',4':6,7]indolizino[1,2-b]quinoline-10,13(9H,15H)-dione without mediated by any spacer.

9. A pharmaceutical composition as claimed in claim 1 or 2 wherein the content of maltose, in terms of the weight as maltose monohydrate, is thrice or more as much as the weight of the compound wherein a polysaccharide derivative having a carboxyl group is bonded to (1S,9S)-1-amino-9-ethyl-5-fluoro-2,3-dihydro-9-hydroxy-4-methyl-1H,12H-benzo [de]pyrano[3',4':6,7]indolizino[1,2-b]quinoline-10,13(9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5-fluoro-2,3-dihydro-9-hydroxy-4-methyl -1H,12H-benzo[de]pyrano[3',4':6,7]indolizino[1,2-b]quinoline-10,13(9H,15H)-dione without mediated by any spacer.

10. A pharmaceutical composition as claimed in claim 2 wherein said pH-adjusting substance is hydrochloric acid or sodium hydroxide.

11. A pharmaceutical composition as claimed in any of claim 1 or 2 which has a pH value of about 5.5 to 9.0.

12. A pharmaceutical composition as claimed in claim 1 or 2 which has a pH value of 6.0 to 9.0.

13. A pharmaceutical composition as claimed in claim 1 or 2 which has a pH value of 6.3 to 7.0.

14. A pharmaceutical composition containing a compound wherein carboxymethyldextran polyalcohol is bonded to (1S,9S)-1-amino-9-ethyl-5-fluoro-2,3-dihydro 9-hydroxy-4-methyl-1H,12H-benzo[de]pyrano[3',4':6,7]indolizino[1,2-b]quinoline-10,13(9H,15H)-dione via a spacer consisting of amino acids represented by the amino acid sequence (N end)-Gly-Gly-Phe-Gly-(C end) and maltose, wherein the molecular weight of said carboxymethyldextran polyalcohol ranges from 50,000 to 500,000, said carboxymethyldextran polyalcohol has a degree of carboxymethylation of from 0.2 to 0.5, (1S,9S)-1-amino-9-ethyl-5-fluoro-2,3-dihydro-9-hydroxy-4-methyl-1H,12H-benzo [de]pyrano[3',4':6,7]indolizino[1,2-b]quinoline-10,13(9H,15H)-dione is introduced in an amount of 2 to 10% by weight based on the weight of said compound, the content of maltose, in terms of the weight as maltose monohydrate, is thrice or more as much as the weight of said compound, and the pH value is from 6.0 to 9.0.

15. A pharmaceutical composition containing a compound wherein carboxymethyldextran polyalcohol is bonded to (1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione via a spacer consisting of amino acids represented by the amino acid sequence (N end)-Gly-Gly-Phe-Gly-(C end), maltose and a pH-adjusting substance, wherein the molecular weight of said carboxymethyldextran polyalcohol ranges from 50,000 to 500,000, said carboxymethyldextran polyalcohol has a degree of carboxymethylation of from 0.2 to 0.5, (1S,9S)-1-amino-9-ethyl-5-fluoro-2,3-dihydro-9-hydroxy-4-methyl-1H,12H-benzo [de]pyrano[3',4':6,7]indolizino[1,2-b]quinoline-10,13(9H,15H)-dione is introduced in an amount of 2 to 10% by weight based on the weight of said compound, the content of maltose, in terms of the weight as maltose monohydrate, is thrice or more as much as the weight of said compound, said pH-adjusting substance is hydrochloric acid or sodium hydroxide, and the pH value is from 6.0 to 9.0.

16. A freeze-dried preparation containing a pharmaceutical composition as claimed in any of claim 1, 2, 14 or 15.

17. A method for preventing aggregation during preservation of a freeze-dried compound wherein a polysaccharide derivative having a carboxyl group is bonded to (1S,9S)-1-amino -9-ethyl-5-fluoro-2,3-dihydro-9-hydroxy-4-methyl-1H,12H-benzo [de]pyrano[3',4':6,7]indolizino[1,2-b]quinoline-10,13(9H,15H)-dione via a spacer consisting of one amino acid or a spacer consisting of 2 to 8 amino acids bonded to each other via peptide bonds, or a compound wherein a polysaccharide derivative having a carboxyl group is bonded to (1S,9S)-1-amino-9-ethyl-5-fluoro-2,3-dihydro-9-hydroxy-4-methyl -1H,12H-benzo [de]pyrano[3',4':6,7]indolizino[1,2-b]quinoline-10,13(9H,15H)-dione without mediated by any spacer, which comprises forming an aqueous solution containing the compound and maltose in an amount sufficient to reduce the aggregation, freeze-drying the solution and preserving the freeze-dried solution.

18. The method of claim 17 wherein the aqueous solution also contains a pH-adjusting substance.

* * * * *